(12) United States Patent
Downey et al.

(10) Patent No.: US 12,017,251 B2
(45) Date of Patent: Jun. 25, 2024

(54) SYSTEM AND METHODS FOR CONTROLLING PATIENT LEAKAGE CURRENT IN A SURGICAL SYSTEM

(71) Applicant: Stryker Corporation, Kalamazoo, MI (US)

(72) Inventors: Adam Darwin Downey, Kalamazoo, MI (US); Patrick Cobler, Nashua, NH (US); Scott Rhodes, North Andover, MA (US)

(73) Assignee: Stryker Corporation, Kalamazoo, MI (US)

( * ) Notice: Subject to any disclaimer, the term of this patent is extended or adjusted under 35 U.S.C. 154(b) by 861 days.

(21) Appl. No.: 16/770,473

(22) PCT Filed: Dec. 4, 2018

(86) PCT No.: PCT/US2018/063775
§ 371 (c)(1),
(2) Date: Jun. 5, 2020

(87) PCT Pub. No.: WO2019/113014
PCT Pub. Date: Jun. 13, 2019

(65) Prior Publication Data
US 2020/0384502 A1 Dec. 10, 2020

Related U.S. Application Data

(60) Provisional application No. 62/595,235, filed on Dec. 6, 2017.

(51) Int. Cl.
*B06B 1/02* (2006.01)
*A61B 17/32* (2006.01)
*A61B 17/00* (2006.01)

(52) U.S. Cl.
CPC .... *B06B 1/0253* (2013.01); *A61B 17/320068* (2013.01); *B06B 1/0246* (2013.01);
(Continued)

(58) Field of Classification Search
CPC . B06B 1/0253; B06B 1/0246; B06B 2201/40; B06B 2201/55; B06B 2201/76;
(Continued)

(56) References Cited

U.S. PATENT DOCUMENTS 3,248,620 A 4/1966 Roland et al.
3,746,897 A 7/1973 Karatjas
(Continued)

FOREIGN PATENT DOCUMENTS

AU 2010300943 B2 11/2013
AU 2013204307 B2 3/2015
(Continued)

OTHER PUBLICATIONS

English language abstract and machine-assisted English translation for CN 1586672 A extracted from espacenet.com database on Feb. 11, 2021, 8 pages.
(Continued)

*Primary Examiner* — Emily P Pham
(74) *Attorney, Agent, or Firm* — Howard & Howard Attorneys PLLC

(57) ABSTRACT

Control consoles and methods for supplying a drive signal to a surgical tool are provided. The control console comprises a transformer with primary and secondary windings. The primary winding receives an input signal from a power source and induces the drive signal in the secondary winding to supply the drive signal to the surgical tool. A first current source comprising a leakage control winding is coupled to a path of the drive signal. The primary winding induces a first cancellation current in the leakage control winding to inject
(Continued)

into the path of the drive signal to cancel leakage current. A sensor coupled to the path of the drive signal outputs a sensed signal to provide feedback related to leakage current. The sensor may connect to a second leakage current cancellation source and/or a fault detection stage. The power source may be variable and may also energize the second current source.

20 Claims, 7 Drawing Sheets

(52) U.S. Cl.
CPC ............ *A61B 2017/00119* (2013.01); *A61B 2017/00199* (2013.01); *B06B 2201/40* (2013.01); *B06B 2201/55* (2013.01); *B06B 2201/76* (2013.01)

(58) Field of Classification Search
CPC .. A61B 17/320068; A61B 2017/00119; A61B 2017/00199; A61B 18/1233
See application file for complete search history.

(56) References Cited

U.S. PATENT DOCUMENTS

| | | | |
|---|---|---|---|
| 3,889,166 A | 6/1975 | Scurlock | |
| 3,946,738 A | 3/1976 | Newton et al. | |
| 3,975,650 A | 8/1976 | Payne | |
| 4,094,320 A | 6/1978 | Newton et al. | |
| 4,231,372 A | 11/1980 | Newton | |
| 4,271,371 A | 6/1981 | Furuichi et al. | |
| 4,336,509 A | 6/1982 | Bernitz | |
| 4,554,477 A | 11/1985 | Ratcliff | |
| 4,642,581 A | 2/1987 | Erickson | |
| 5,136,199 A | 8/1992 | Kawai | |
| 5,152,762 A | 10/1992 | McElhenney | |
| 5,318,563 A | 6/1994 | Malis et al. | |
| 5,372,596 A | 12/1994 | Klicek et al. | |
| 5,394,047 A | 2/1995 | Scharlack et al. | |
| 5,930,121 A | 7/1999 | Henry | |
| 6,245,063 B1 | 6/2001 | Uphoff | |
| 6,398,781 B1 | 6/2002 | Goble et al. | |
| 6,819,027 B2 | 11/2004 | Saraf | |
| 7,160,020 B2 | 1/2007 | Sand | |
| 7,794,414 B2 | 9/2010 | Rabiner et al. | |
| 7,857,783 B2 | 12/2010 | Kadziauskas et al. | |
| 8,115,366 B2 | 2/2012 | Hoffman et al. | |
| 8,197,502 B2 | 6/2012 | Smith et al. | |
| 8,236,020 B2 | 8/2012 | Smith et al. | |
| 8,439,416 B2 | 5/2013 | Lambarth et al. | |
| 8,475,446 B2 | 7/2013 | Daw et al. | |
| 8,551,088 B2 | 10/2013 | Falkenstein et al. | |
| 8,624,606 B2 | 1/2014 | Gilbert | |
| 8,669,809 B2 | 3/2014 | Ikriannikov et al. | |
| 8,864,205 B2 | 10/2014 | Lemire et al. | |
| 8,956,349 B2 | 2/2015 | Aldridge et al. | |
| 8,973,963 B2 | 3/2015 | Lambarth et al. | |
| 9,060,775 B2 | 6/2015 | Wiener et al. | |
| 9,072,539 B2 | 7/2015 | Messerly et al. | |
| 9,319,008 B2 | 4/2016 | Ikriannikov et al. | |
| 9,456,939 B2 | 10/2016 | Lambarth et al. | |
| 9,615,983 B2 | 4/2017 | Stryker et al. | |
| 10,022,567 B2 | 7/2018 | Messerly et al. | |
| 10,022,568 B2 | 7/2018 | Messerly et al. | |
| RE47,996 E * | 5/2020 | Turner | A61N 7/00 |
| 11,673,163 B2 * | 6/2023 | Downey | A61B 17/320068 |
| | | | 310/317 |
| 2005/0253536 A1 | 11/2005 | Oyama | |
| 2007/0247877 A1 | 10/2007 | Kwon et al. | |
| 2007/0249941 A1 | 10/2007 | Salehi et al. | |
| 2009/0088737 A1 | 4/2009 | Daw et al. | |
| 2010/0102672 A1 | 4/2010 | Hoffman et al. | |
| 2010/0125292 A1 | 5/2010 | Wiener et al. | |
| 2010/0318079 A1 | 12/2010 | McPherson et al. | |
| 2011/0087212 A1 | 4/2011 | Aldridge et al. | |
| 2011/0215807 A1 | 9/2011 | Misic et al. | |
| 2011/0241576 A1 | 10/2011 | Paschke | |
| 2012/0078139 A1 | 3/2012 | Aldridge et al. | |
| 2012/0172866 A1 | 7/2012 | Behnke, II | |
| 2012/0221031 A1 | 8/2012 | Smith et al. | |
| 2012/0265196 A1 * | 10/2012 | Turner | H01H 1/00 |
| | | | 606/34 |
| 2013/0035679 A1 | 2/2013 | Orszulak | |
| 2013/0345695 A1 | 12/2013 | McPherson | |
| 2014/0049299 A1 | 2/2014 | Chu | |
| 2014/0080413 A1 | 3/2014 | Hayes et al. | |
| 2014/0139313 A1 | 5/2014 | Zhou et al. | |
| 2015/0098307 A1 | 4/2015 | Lei et al. | |
| 2015/0105767 A1 | 4/2015 | Johnson et al. | |
| 2016/0022348 A1 | 1/2016 | Bales, Jr. et al. | |
| 2016/0030104 A1 | 2/2016 | Gilbert et al. | |
| 2016/0302848 A1 | 10/2016 | Krapohl | |
| 2016/0367416 A1 | 12/2016 | Lambarth et al. | |
| 2017/0000542 A1 | 1/2017 | Yates et al. | |
| 2017/0027029 A1 | 1/2017 | Hu et al. | |
| 2017/0071621 A1 | 3/2017 | Downey et al. | |
| 2017/0086913 A1 | 3/2017 | Yates et al. | |
| 2017/0143369 A1 | 5/2017 | Downey et al. | |
| 2017/0146584 A1 | 5/2017 | Daw et al. | |
| 2017/0151011 A1 | 6/2017 | Brustad et al. | |
| 2018/0036030 A1 | 2/2018 | Pantano | |
| 2019/0291135 A1 | 9/2019 | Downey | |

FOREIGN PATENT DOCUMENTS

| | | |
|---|---|---|
| CN | 1225757 A | 8/1999 |
| CN | 1586672 A | 3/2005 |
| CN | 102332447 A | 1/2012 |
| CN | 105099212 A | 11/2015 |
| CN | 204767038 U | 11/2015 |
| EP | 2283788 A1 | 2/2011 |
| EP | 2470140 A2 | 7/2012 |
| EP | 2537499 A2 | 12/2012 |
| EP | 2777577 A1 | 9/2014 |
| EP | 2895130 A1 | 7/2015 |
| EP | 3177217 A1 | 6/2017 |
| GB | 2090705 A | 7/1982 |
| GB | 2448585 A | 10/2008 |
| JP | S5853195 A | 3/1983 |
| JP | H04066301 A | 3/1992 |
| JP | H0747080 A | 2/1995 |
| JP | 2004364344 A | 12/2004 |
| JP | 5552167 B2 | 7/2014 |
| WO | 9804029 A1 | 1/1998 |
| WO | 2011041170 A2 | 4/2011 |
| WO | 2014043659 A1 | 3/2014 |
| WO | 2015021216 A1 | 2/2015 |
| WO | 2016022808 A1 | 2/2016 |
| WO | 2016183084 A1 | 11/2016 |
| WO | 2017011619 A1 | 1/2017 |
| WO | 2017106329 A1 | 6/2017 |
| WO | 2017210076 A2 | 12/2017 |

OTHER PUBLICATIONS

English language abstract and machine-assisted English translation for CN 105099212 A extracted from espacenet.com database on Feb. 11, 2021, 13 pages.

English language abstract and machine-assisted English translation for JPH 04-066301 A extracted from espacenet.com database on Mar. 17, 2023, 4 pages.

English language abstract and machine-assisted English translation for JPH 07-47080 A extracted from espacenet.com database on Mar. 17, 2023, 9 pages.

English language abstract for JP 5552167 extracted from espacenet.com database on Jan. 28, 2019, 2 pages.

Gentile, Ken, "Driving a Center-Tapped Transformer with a Balanced Current-Output DAC", Analog Devices, AN-912, Application Note, 2007, pp. 1-12.

(56) References Cited

OTHER PUBLICATIONS

International Search Report for Application No. PCT/US2016/031651 dated Oct. 10, 2016, 7 pages.
International Search Report for Application No. PCT/US2017/034437 dated Jan. 26, 2018, 4 pages.
International Search Report for Application No. PCT/US2018/0633775 dated Mar. 27, 2019, 5 pages.
Invitation to Pay Additional Fees—Communication Relating to the Results of the Partial International Search for Application No. PCT/US2017/034437 dated Nov. 3, 2017, 3 pages.
Machine-assisted English translation for JPS 58-53195 extracted from PAJ database on Dec. 6, 2017, 3 pages.
Svilanis, G., et al., "Power Amplifier for Ultrasonic Transducer Excitation", ISSN 1392-2114, ULTRAGARSAS, No. 1(58), 2006, pp. 30-36.
English language abstract and machine-assisted English translation for CN 204767038 U extracted from espacenet.com database on Jan. 3, 2024, 15 pages.
English language abstract and machine-assisted English translation for JP 2004-364344 A extracted from espacenet.com database on Jan. 3, 2024, 8 pages.
English language abstract for CN 1225757 A extracted from espacenet.com database on Apr. 3, 2024, 2 pages.
English language abstract and machine-assisted English translation for CN 102332447 A extracted from espacenet.com database on Apr. 3, 2024, 12 pages.

* cited by examiner

SYSTEM AND METHODS FOR CONTROLLING PATIENT LEAKAGE CURRENT IN A SURGICAL SYSTEM

CROSS-REFERENCE TO RELATED APPLICATION

The subject patent application is the National Stage of International Patent Application No. PCT/US2018/063775, filed on Dec. 4, 2018, which claims priority to and all the benefits of U.S. Provisional Patent Application No. 62/595,235 filed on Dec. 6, 2017, the disclosures of which i-sare hereby incorporated by reference in it-stheir entirety.

TECHNICAL FIELD

The present disclosure generally relates to control consoles that supply drive signals to electrically powered surgical tools, and more specifically, that are designed to reduce patient leakage current of/from drive signals.

BACKGROUND

A powered surgical tool system can be considered to have three basic components. A control console produces drive signals that have the characteristics necessary to actuate the second component of the system, the power generator. The power generator converts the electrical energy of the drive signals into another form of energy. The types of energy into which the electrical energy is converted include, mechanical energy, thermal energy (heat) and photonic (light) energy. The third component of the tool system is the energy applicator. The energy applicator receives the energy output by the power generator and applies this energy to the targeted tissue to perform a specific therapeutic task. Some tool systems are designed to apply electrical energy directed to the targeted tissue. In this type of system, the power generator is essentially the conductors over which the drive signals are applied to the exposed electrodes over which the current is sourced to the tissue. The electrodes function as the energy applicator. Electrodes may be placed on a patient or integrated into a hand piece. Other tool systems are designed to provide mechanical energy. In this type of system, the power generator converts electrical energy, e.g. an AC drive signal, into mechanical energy, e.g. vibrations, which are applied to the patient through the hand piece.

An integral part of many surgical tool systems is the surgical tool, which can be a hand piece. At a minimum, the hand piece is the physical component designed to be held by the practitioner from which the energy applicator extends. Often the power generator is contained in the surgical tool. One such surgical tool system so designed is an ultrasonic surgical tool system. The surgical tool of this system includes a power generator that includes one or more drivers. Each driver, in response to the application of an AC signal, vibrates. A horn is closely mechanically coupled to the drivers. A tip, which functions as the energy applicator, extends distally from the horn. The vibrations of the drivers foster like vibrations in the horn and, by extension, the tip. The motion of a vibrating tip against tissue results in the ablation of, the removal of, the tissue.

An inherent characteristic many powered surgical tool systems share with other electrically powered assemblies is that parasitic capacitances are present across the components of these systems. A parasitic capacitance is the capacitance present across two components that are at unequal voltages. A consequence of the presence of this capacitance is that a parasitic alternating current can flow through one of the components. For example, when a surgical tool includes a power generating unit to which AC drive signals are applied, due to the parasitic capacitance between the metal structural components of the surgical tool and the power generating components internal to the surgical tool through which current flows, a parasitic current can flow through the metal structural components. This parasitic current contributes to what is known as leakage current. Generally, leakage current is the unintended flow of current through the components of a system to which a current is applied for other purposes. Patient leakage current, more specifically, is the unintended flow of current through a patient.

There is a possibility that a patient can inadvertently be connected to earth ground during a procedure. If this event does occur, leakage current can flow from the surgical tool into the patient. To avoid danger to the patient, the powered surgical tool system should be designed to minimize leakage current that flows through the patient, such as in a scenario where the patient becomes earth grounded. If a surgical tool through which a leakage current could be present is applied to the patient, the leakage current can, in theory, flow through the patient to this ground. This current can adversely affect the functioning of the patient's organs and tissue.

For these reasons, a surgical tool system with a surgical tool intended for application to the patient is designed to ensure that the normal leakage current flow is less than 100 µAmps. A surgical tool system with a surgical tool intended for application to cardiac tissue must be designed so the normal leakage current flow is less than 10 µAmps if it will be used in the United States. These requirements are based on the IEC 60601 Medical Design Standards. The IEC 60601 Standards also describe the process for testing a powered surgical tool to ensure the leakage current is below these maximum amounts.

It is a further requirement that a tool applied to a patient cannot function as a connection to ground. Mainly, if a voltage from another source is somehow applied to the patient, the tool should not function as a connection to ground resulting in a current flow through the patient.

Powered surgical tool systems may have outputs that are isolated from ground to prevent current leakage. However, isolated output circuits are, by themselves, not enough to reduce leakage to acceptable levels. Some powered surgical tool systems have been designed with the capability of detecting open circuits and being able to lower their peak output voltage accordingly. This leads to several performance problems. Lowering peak output voltage in order to minimize leakage current may degrade the performance of the tool system since the peak output voltage initiates the sparking needed for proper coagulation effect. Further, the amount of time needed by the generator to sense the open circuit condition may lead to momentary voltage spikes, which could allow leakage current to occur.

One method is to reduce the parasitic capacitance to reduce the parasitic current flow. If the tool is an ultrasonic surgical tool, parasitic capacitance can be reduced by providing electrically insulating impedance disks between the drivers and the horn that the mechanical components of the surgical tool that are intended to be vibrated by the drivers. A disadvantage associated with providing these disks is that they damp the transfer of vibrations from the drivers to the horn and tip. This mechanical damping reduces the efficiency of the surgical tool.

As such, there is a need to address at least the aforementioned technical deficiencies of prior systems and methods.

SUMMARY

In one embodiment, a control console for supplying a drive signal to a surgical tool, and methods of operating the same, are provided. The control console comprises a transformer including a primary winding and a secondary winding. The primary winding is configured to receive an input signal from a power source and to induce the drive signal in the secondary winding to supply the drive signal to the surgical tool. The control console further comprises a first current source comprising a leakage control winding coupled to a path of the drive signal and with the primary winding configured to induce a first cancellation current in the leakage control winding to inject into the path of the drive signal to cancel leakage current of the drive signal. The control console also includes a sensor coupled to the path of the drive signal, wherein the sensor is configured to output a sensed signal to provide feedback related to leakage current.

In another embodiment, a control console for supplying a drive signal to a surgical tool, and methods of operating the same, are provided. The control console comprises a transformer including a primary winding and a secondary winding. The primary winding is configured to receive an input signal from a power source and to induce the drive signal in the secondary winding to supply the drive signal to the surgical tool. The control console further comprises a first current source comprising a leakage control winding coupled to a path of the drive signal and with the primary winding configured to induce a first cancellation current in the leakage control winding to inject into the path of the drive signal to cancel leakage current of the drive signal. A sensor is configured to sense a characteristic of the input signal and to output a sensed signal related to the characteristic of the input signal. A second current source is coupled to the path of the drive signal. A variable gain device is coupled to the sensor and to the second current source. A selection interface is coupled to the second current source and to the variable gain device and is configured to enable selection of one of a plurality of leakage current adjustment settings and to provide selected leakage current adjustment setting to the variable gain device. The variable gain device is configured to receive the sensed signal and to modify the sensed signal based on the selected leakage current adjustment setting. The second current source is configured to generate a second cancellation current based on the modified sensed signal from the variable gain device and to inject the second cancellation current into the path of the drive signal to cancel leakage current of the drive signal.

In another embodiment, a control console for supplying a drive signal to a surgical tool, and methods of operating the same, are provided. The control console comprises a variable power source, a transformer and a current source. The transformer comprises a primary winding and a secondary winding. The primary winding is coupled to the variable power source and is configured to receive an input signal from the variable power source and to induce a drive signal in the secondary winding to supply the drive signal to the surgical tool. The current source is coupled to a path of the drive signal and is coupled to the variable power source. The variable power source is configured to energize the current source. The current source is configured to generate a cancellation current to inject into the path of the drive signal to cancel leakage current of the drive signal.

These embodiments offer multiple advantages including enabling the control console to maintain low leakage current without the use of cumbersome additional devices that decrease the output power of the surgical tool, providing the ability to monitor the drive signal for leakage current-which enables the addition of further leakage control and fault detection stages, and/or simplification of the control console by using a single power source to energize the drive signal and leakage control sources. Additional advantages of the control console and methods described herein, as well as the embodiments of the same, will be understood in reference to the description provided herein.

BRIEF DESCRIPTION

Advantages of the present invention will be readily appreciated as the same becomes better understood by reference to the following detailed description when considered in connection with the accompanying drawings wherein.

DETAILED DESCRIPTION

I. Overview

Figure 1:
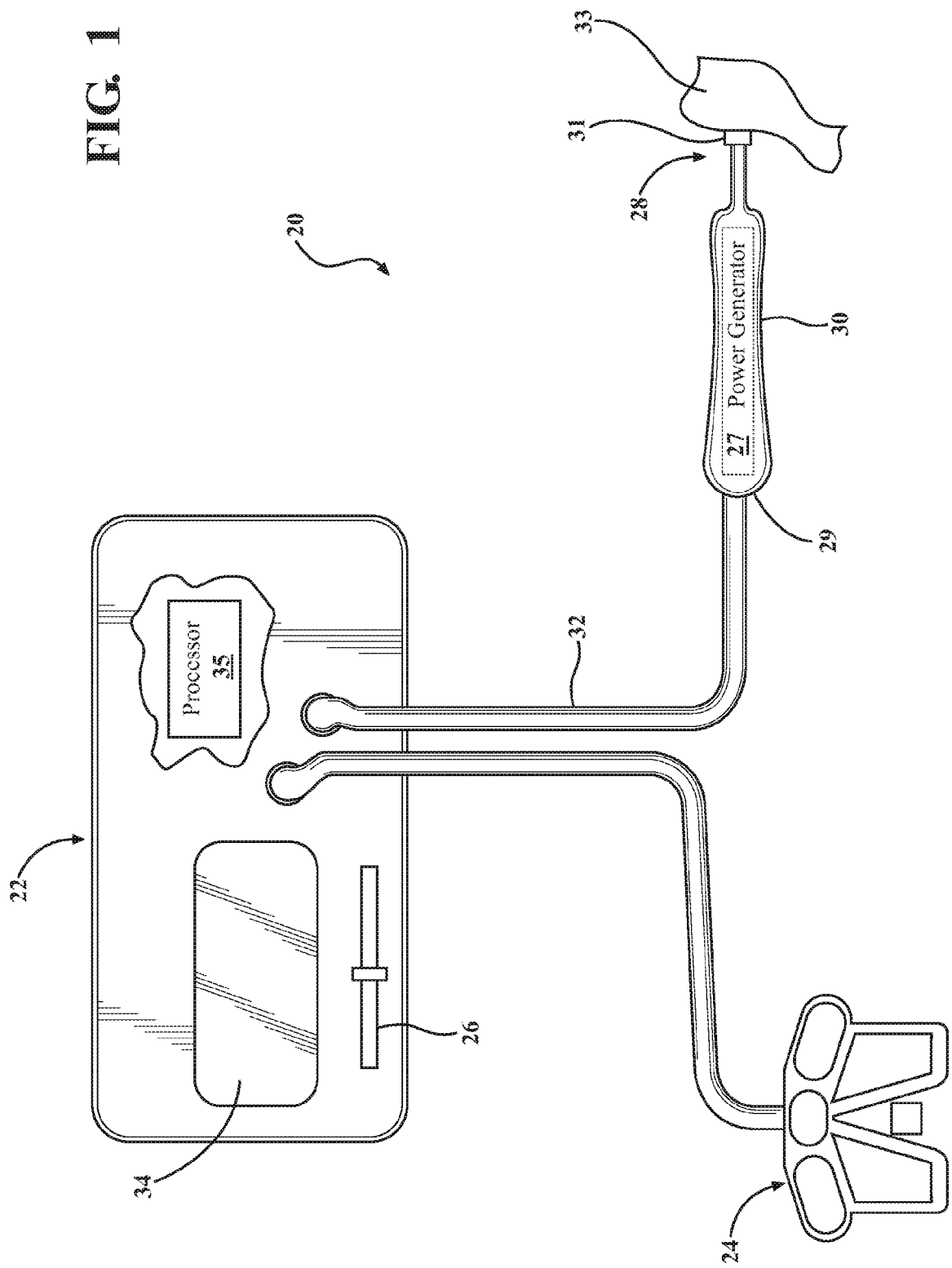
FIG. 1 depicts a one embodiment of a powered surgical tool system comprising a control console and a surgical tool.

Referring to the Figures, wherein like numerals indicate like or corresponding parts throughout the several views, a powered surgical tool system 20 is provided having a control console 22 configured to supply a drive signal 105 to a surgical tool 28.

Reference will now be made to the embodiments illustrated in the drawings and specific language will be used to describe the same. No limitation of the scope of the disclosure is intended by using specific language to describe exemplary embodiments. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

The powered surgical tool system 20 is now generally described by reference to FIG. 1 and is hereinafter referred to as "the system 20" for simplicity. The system 20 includes the surgical tool 28. The surgical tool 28 can be an ultrasonic surgical tool or tool for application of RF or other type of electrosurgical energy. The surgical tool 28 may include a shell or body 30. The body 30 is the portion of the surgical tool 28 that is actually held by the medical practitioner. The body 30 forms a proximal end 29 of the surgical tool. The term "proximal" is understood to mean closer to the practitioner holding the surgical tool, and further away from the site 33 to which the surgical tool 28 is applied. A distal end 31 of the surgical tool 28 is located opposite the proximal end 29. The term "distal" is understood to mean further away from the practitioner, and closer to the site 33 to which the surgical tool 28 is applied.

The control console 22 is part of system 20. Control console 22 sources drive signals 105 (described below) over a cable 32 to which the surgical tool 28 is connected. In embodiments in which the surgical tool 28 is an ultrasonic surgical tool, it is desirable, but not required, to assemble the cable 32 and the surgical tool 28 as a single unit. The control console 22 includes components that function as a signal generator. These components produce the drive signal 105, e.g., an AC signal, that is applied to a power generator 27 of the surgical tool 28. The power generator 27, also referred to as a transducer, converts the AC signal to the type of surgical energy to be applied to the patient. For example, in an ultrasonic surgical tool 28 the power generator 27 may be a piezo electric stack that converts electrical energy into vibrations. Alternatively, in an RF surgical tool 28 the power generator 27 may not be needed as electrical energy is applied directly to the patient through electrodes. The surgical tool 28 depicted in FIG. 1 is configured to apply ultrasonic or RF energy to the patient through the tip of the surgical tool at the distal end 31. Surgical energy may also be applied to patient tissue 33 through an electrode or other surgical tools other than those described herein. Regardless of the type of energy applied, the control console 22 is designed to minimize the potential for current leakage into the patient.

A control interface 24 is connected to control console 22. In FIG. 1, the control interface 24 is a foot pedal. A state of control interface 24 is monitored by a processor 35 within the control console 22. The control interface 24 is a user actuated control member that regulates activation and/or specific control of the surgical tool 28 through the control console 22. In FIG. 1, the control interface 24 is shown as being part of a foot pedal assembly that includes several pedals. The added pedals may be used to control devices such as irrigation pump, a suction pump or a light. The control interface 24 may comprise configurations other than the foot pedal as depicted in FIG. 1.

The control console 22 may further include a user interface 26, such as a Graphical User Interface or switch. Like the control interface 24, the user interface 26 is monitored by the processor 35 within the control console 22. The user interface 26 is controlled by the practitioner to control operating parameters for the surgical tool 28. In ultrasonic embodiments, such operating parameters may include the magnitude of the amplitude of the vibrations of surgical tool 28.

The control interface 24 and user interface 26 are understood to be general representations of the means of inputting commands to system 20. In some constructions of the system 20, a single control unit may perform both functions. For example, the system 20 may be configured so that when a lever or foot pedal is initially first depressed, the system 20 causes a tip head of the surgical tool 28 to undergo a vibration cycle that is of relatively small amplitude. As a result of the continued depression of the lever or foot pedal, the control console 22 resets the drive signal 105 applied to the surgical tool 28 so as to cause tip head to undergo vibration cycles that are of a larger magnitude.

The control console 22 may include a display 34. Images on the display 34 may be generated by the processor 35 with the control console 22. Information depicted on display 34 includes, but is not limited to, information related to the user interface 26, information identifying the surgical tool 28 and the tip, and any other information describing operation, settings, or notifications of the system 20. The display 34 may be a touch screen display. In these versions, by depressing images of buttons presented on the display 34, command can be entered into the processor 35 within the control console 22. Any suitable interface components between the display 34 and the processor 35 may be provided to facilitate presentation of images on the display 34 and the entry of commands into the processor 35. Additional details regarding a processor which may be used with the embodiments disclosed are included in PCT Pat. App. No. PCT/US2016/031651, the contents of which are contained in WO 2016/183084 A1/US Pat. Pub. No. 2018/0056328 A1, the contents of which are herein incorporated by reference in their entirety.

The processor 35 regulates the outputting of drive signals 105 from the control console 22. The practitioner-controlled inputs upon which the processor 35 sets the drive signals 105 may be based on the state of the control interface 24 and/or the user interface 26. Commands entered through the display 34 may also be used to control the setting of the drive signal 105. The characteristics of the drive signal 105 may also set based on data read from the surgical tool 28 memory. The characteristics of the drive signals 105 are also employed by the control console 22 as feedback signals that further contribute to the setting of the drive signal 105. Based on these plural inputs, processor 35 outputs the signals that control the drive signal 105.

Referring to FIGS. 4-7, the control console 22 includes, or is otherwise coupled to, a power source 82. The power source 82 is configured to apply an input signal to a primary winding 84 of a transformer 90. The input signal from the power source 82 is applied to a center tap of the primary winding 84 of the transformer 90. Transformer 90 electrically isolates the patient side circuitry from the power source 82. The transformer 90 blocks any DC component of the signal in primary winding 84 from transferring to secondary winding 88 and may be designed with insulation, shown in FIGS. 4-7 as a core 98, to minimize capacitive coupling.

The opposed taps of the primary winding 84 are each coupled to a linear amplifier 86. Each amplifier 86 applies AC signals that vary in both potential and frequency to the taps of the primary winding 84. A base signal applied to amplifier 86 as a control signal regulates the frequency and potential of the signals output by the amplifier 86. In an embodiment in which system 20 includes an ultrasonic surgical tool 28, the AC signal that is developed across the primary winding 84 may have a frequency between 10 kHz and 100 kHz. This signal may have a peak to peak voltage of at least 200 Volts and more. For other applications, such as RF treatment, the AC signal may have frequency and voltage ranges other than those described herein.

The structure of the power source 82 and the linear amplifier 86 are not limited to the specific embodiments shown herein, and may include different configurations for generating an AC signal over the primary winding 84. A further understanding of these sub-assemblies can be found in PCT Pat. App. No. PCT/US2016/031651, the contents of which are contained in WO 2016/183084 A1/US Pat. Pub. No. 2018/0056328 A1, the contents of which are herein incorporated by reference in their entirety.

The AC signal that develops across the primary winding 84 induces an AC signal across the secondary winding 88 of the transformer 90. This signal across the secondary winding 88 of transformer 90 is the drive signal 105 applied over cable 32 to the power generator 27 within surgical tool 28. Cable 32 contains a high voltage conductor 100 with high potential current that flows toward the surgical tool 28 and a low voltage conductor 102 with low potential current that flows away from the surgical tool 28. A path 104 of the drive signal (also referred to as "drive path") is defined by these conductors 100, 102. The drive signal 105 is the current that runs through the drive path 104. In an embodiment in which the drive signal 105 is used to actuate ultrasonic drivers, the drive signal has a voltage of at least 500 VAC and can be over 1000 VAC.

The drive path 104 is surrounded by a shield 99. The shield 99 prevents parasitic capacitance between the high voltage conductor 100 and earth ground or any objects near the drive path 104. In addition, the shield may be coupled to the low voltage conductor 102 within the surgical tool 28. In embodiments where this connection is present, the shield 99 also acts as a secondary path for the return current and protects the patient in the event there is a break in the low-voltage conductor 102.

II. Techniques for Leakage Current Detection and Cancellation

According to the techniques described herein, the system 20 may employ leakage cancellation techniques for cancelling patient leakage current (also referred to as "leakage current"). Leakage current is generally the current that flows through a patient connected to the surgical tool 28. Leakage current can flow from the control console 22, to the surgical tool 28, through the patient and to earth ground. As such, the leakage current is generally unintended flow of electrical current through the patient.

As will be understood from the examples described herein, the system 20 may employ leakage current cancellation using active control, or using a combination of active and passive control. Active controlled techniques employ elements that make determinations based on input or feedback signals. Passive controlled techniques employ elements, such as transformers, resistors, capacitors, inductors, that passively provide leakage current cancellation without active determinations. Active controlled techniques may include passive elements to supplement active devices. One or more of these active and passive leakage current cancellations systems may be included in the control console 22.

Figure 3:
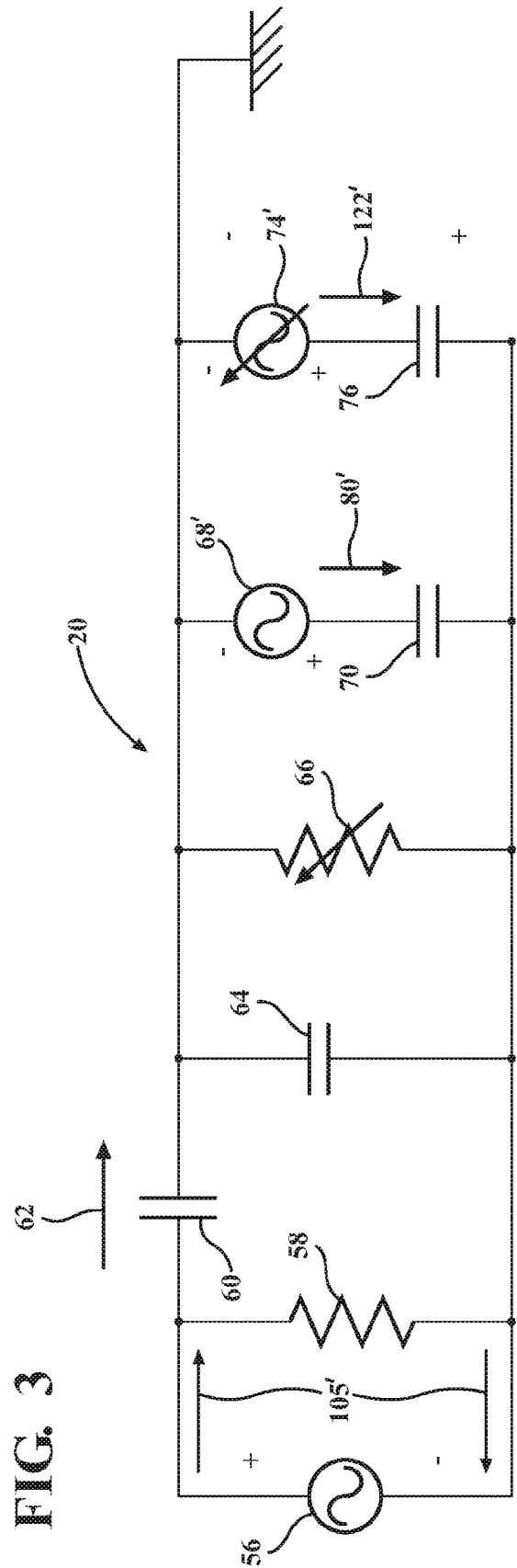
FIG. 3 is a schematic representation of two sources for cancelling leakage current for the powered surgical tool system, according to one example.

In one embodiment shown in FIG. 3, an equivalent circuit is provided illustrating operation of a first source 68' and a second source 74' for cancelling leakage current. The first source 68' is a passive-type and is depicted as an AC voltage source. The second source 74' is an active-type and is depicted as a variable AC voltage source. The first source 68' produces a first cancellation current 80' and the second source 74' produces a second cancellation current 122'. Hence, the first and second sources 68', 74' are current sources, in that these sources 68', 74' produce cancellation currents 80', 122', respectively, as illustrated by FIG. 3. Sources 68', 74' are referred to herein as current sources.

A power source representation 56 (comprising the power source 82 and transformer 90) generates the drive signal 105 for the surgical tool 28. The cancellation currents 80', 122' are injected by these sources 68', 74' into the drive signal 105, or into the path 104 of the drive signal 105.

In this equivalent schematic, the first current source 68' is illustrated in series with capacitor 70 and the second current source 74' is in series with capacitor 76. Impedance 58 represents a known impedance of the surgical tool 28, resistor 66 represents a variable impedance through the surgical site 33, and capacitors 60 and 64 represent capacitances for the high and low side voltage conductors 100, 102, respectively. Such capacitances may be parasitic, thereby resulting in generation of the leakage current 62'. In this example, leakage current 62' in the drive signal 105 is traveling through capacitor 60.

According to IEC 60601 Medical Design Standards, the powered surgical tool system 20 shall maintain the leakage current at 100 µAmps or less. If the powered surgical tool system 20 is designed for use on or near cardiac tissue, a maximum leakage current is 10 µAmps.

In some embodiments, the first current source 68' is designed to cancel a majority (e.g., 50%-90%) of the leakage current 62'. The second current source 74' generates the second cancellation current 122' to cancel at least some of the residual leakage current 62' that remains after cancellation by the first cancellation current 80'. Such residual leakage current 62' may be 1-40% of the total leakage current 62', for example. In one example, the first current source 68 may be designed to cancel up to ±500 µA patient leakage current cancellation, while leaving a small amount of residual leakage current, e.g. ±40 µA patient leakage current. In other examples, the second current source 74' may cancel a majority of the leakage current 62'.

In an ideal control console 22, leakage current 62' of the drive signal 105 will be equal to the first cancellation current 80' plus the second cancellation current 122'. Alternative embodiments may use a single active or passive current source, any combination of active and/or passive current injection sources, or any pluralities thereof.

As will be appreciated from the embodiments described herein, the second (active) current source 74 may comprise additional components beyond those components that actually generate the second cancellation current 122. Such additional components, may, for example, aide in determining how or when to produce the second cancellation current 122. As such, the phrase "second current source" as described herein, is not limited solely to current generating components.

Referring now to FIGS. 4-7, further aspects of the first current source 68 and second current source 74 are described. The first current source 68 may also be referred to as a matched current source. The first current source 68, according to one embodiment, comprises a leakage control winding 92. The leakage control winding 92 may also be referred to as tuned winding or a sense winding. The leakage control winding 92 may be integrated with the transformer 90 such that the transformer 90 includes the leakage control winding 92. Examples of how the leakage control winding 92 and capacitor 94 can both be made integral with the transformer 90 are described in PCT App. No. PCT/US2017/034437, the contents of which are published in PCT Pub. No. WO 2017/210076 A2/US Pat. Pub. No. 2019/0291135 A1, the contents of which are hereby incorporated by reference in their entirety. The first current source 68 may also include a capacitor 94.

Figure 4:
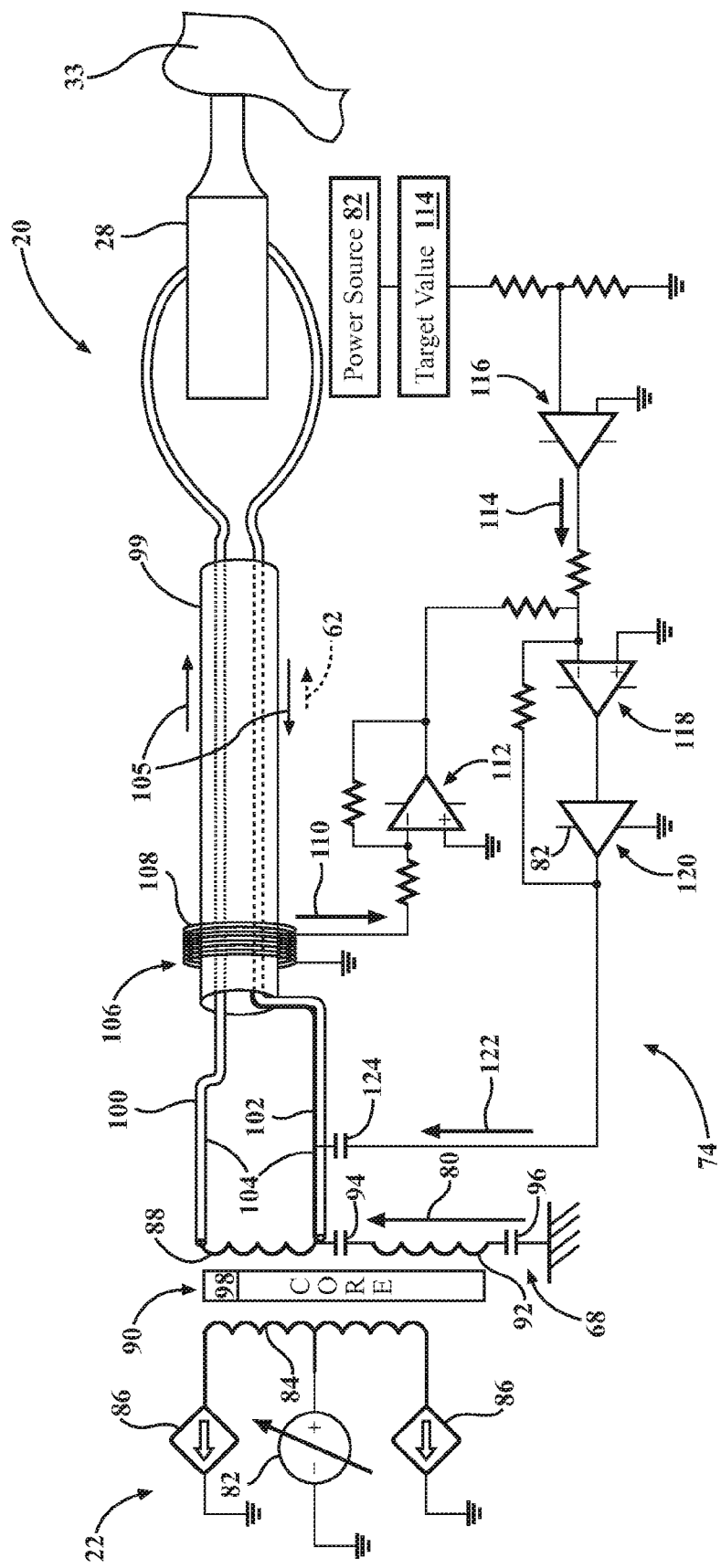
FIG. 4 is a schematic diagram of an embodiment of the powered surgical tool system comprising the control console with two leakage current cancellation stages and current-based sensing of leakage current.

Current is induced across the leakage control winding 92 by the primary winding 84. Induction of this current facilitates generation of the first cancellation current 80 by the first current source 68. The first cancellation current 80 is injected into the low side voltage conductor 102 of the drive signal path 104. While FIG. 4 shows the first cancellation current 80 injected into the low-side voltage conductor 102, cancellation current of opposite polarity could be injected into the high-side voltage conductor 100 to offset leakage current 62'. In embodiments where the control console 22 includes the transformer 90 across which the drive signal 105 is generated, one or all of the components forming the first current source 68 may be built into a single unit with the transformer 90.

Additional details regarding the structure of the transformer 90 and the first current source 68 may be found in PCT App. No. PCT/US2017/034437, the contents of which are published in PCT Pub. No. WO 2017/210076 A2/US Pat. Pub. No. 2019/0291135 A1, the contents of which were previously incorporated by reference.

A. Closed Loop Leakage Current Cancellation Control

Referring to FIGS. 2, 4, 5 and 7, embodiments of second current sources 74 employed by the control console 22 to cancel at least some of the leakage current 62 are described. In one example, the second current sources 74 utilize feedback signals, which can be a measurement of current or voltage of the drive signal 105, to cancel at least some of the leakage current 62.

Figure 2:
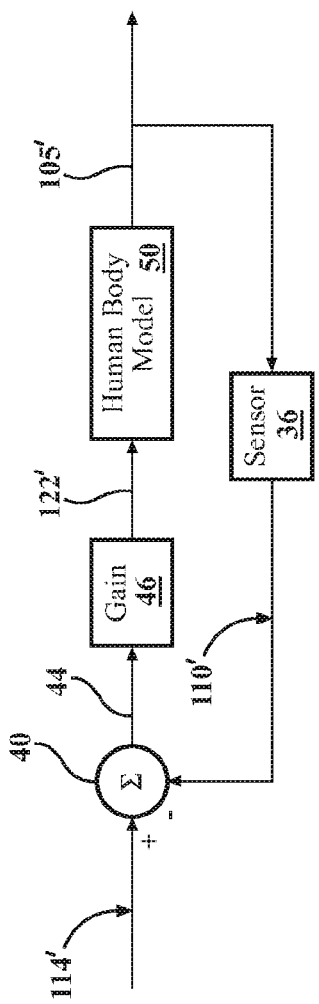
FIG. 2 is a diagram of the operation of a feedback loop for measurement and cancellation of leakage current, according to one example.

Cancellation of leakage current 62 through the use of a feedback signal is illustrated in the control loop shown in FIG. 2. One or more sensors 36 measure a characteristic the drive signal 105 and output a sensed signal 110' related to leakage current 62. The sensed signal 110' may be current, voltage, or any property bearing a known or determinable relationship to leakage current 62. A target value 114' is set and may be 0 or any other positive or negative value. The target value 114' may be a target signal including a current amplitude, or a voltage. The target value 42 may include both AC and DC components. The difference between the sensed signal 110' and the target value 114' is determined to produce an error signal 44. In an embodiment, the error signal 44 is calculated by a summation stage 40 by summing the positive target value 114' with the negative of the sensed signal 110'. Many additional ways to determine the difference between a sensed signal 110' and target value 114' could be substituted for this summing process.

The error signal 44 is multiplied by a gain device 46. The gain device 46 may increase, decrease, or allow the error signal 44 to remain the same. The gain device 46 may be circuitry, software, or a combination of the two. The gain device 46 outputs the cancellation current 122' that is injected into the drive signal 105' to offset the leakage current 62. The human body model 50, which represents the surgical tool 28 applied to a patient, is powered by the drive signal 105, which includes the cancellation current 122'. The transfer function of the control loop may be represented as: TF=G/(1+S*G). Where G represents the gain 46 and S is the sensed signal 110'. The principles illustrated by FIG. 2 are implemented in embodiments of the surgical system 20 shown in FIGS. 4, 5 and 7.

Figure 5:
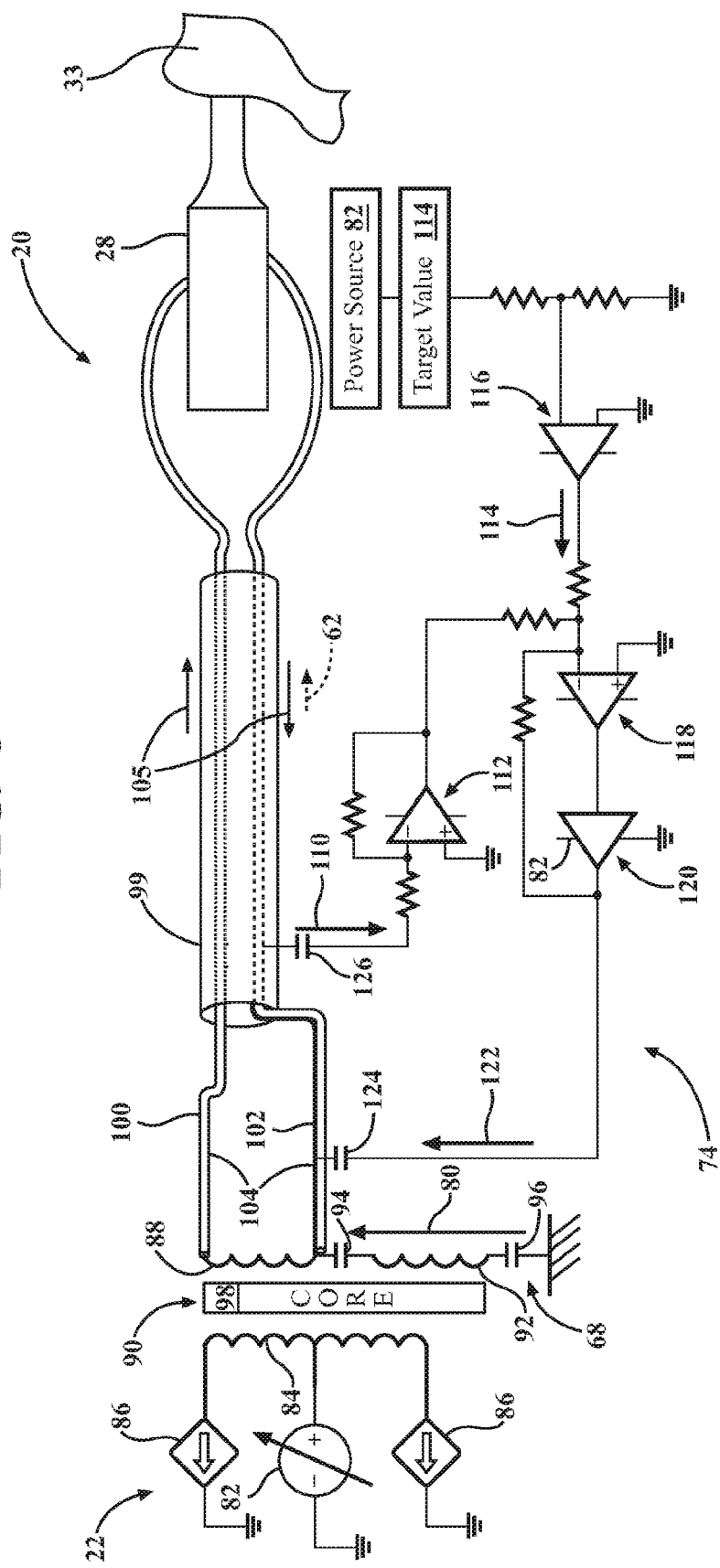
FIG. 5 is a schematic diagram of another embodiment of the powered surgical tool system comprising the control console with two leakage current cancellation stages and voltage-based sensing of a drive signal.
Figure 6:
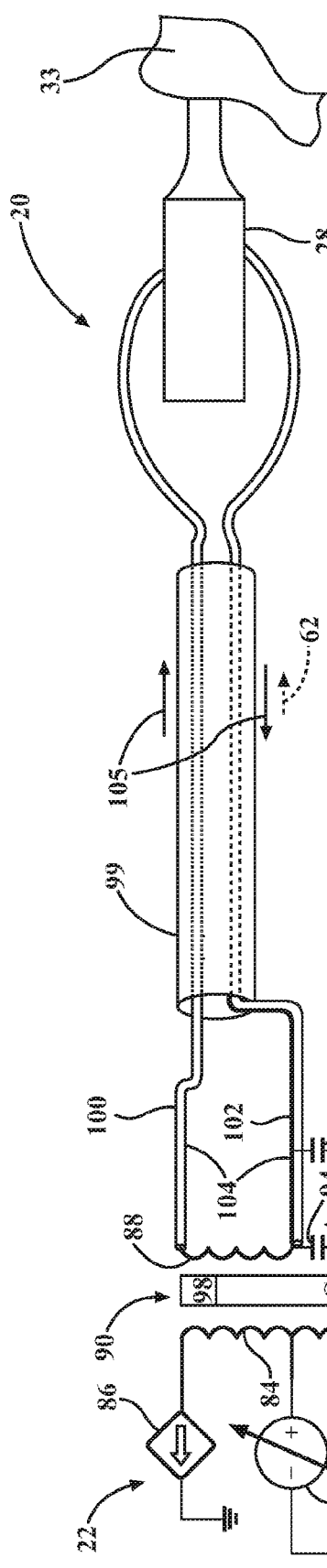
FIG. 6 is a schematic diagram of an alternative embodiment of another embodiment of the powered surgical tool system comprising the control console with two leakage current cancellation stages and techniques for adjusting leakage current settings.
Figure 6:
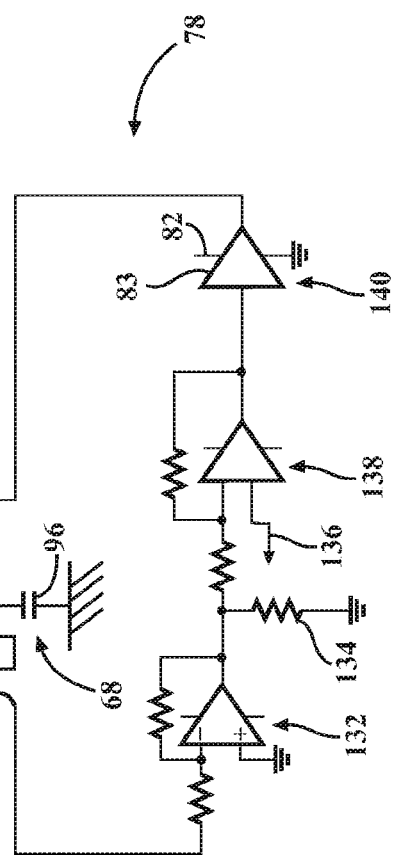
Figure 7:
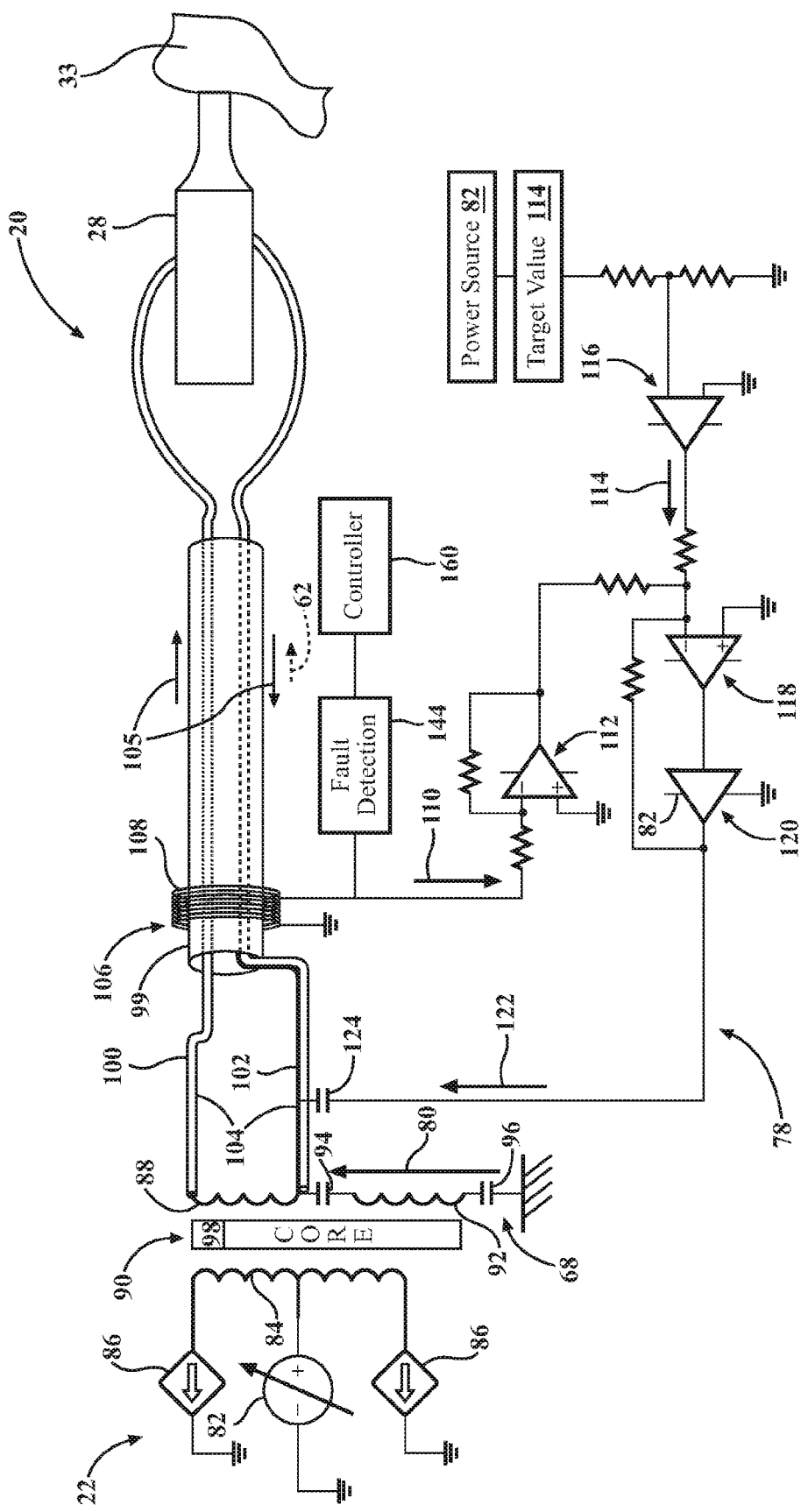
FIG. 7 is a schematic diagram of another embodiment of the powered surgical tool system comprising the control console with two leakage current cancellation stages and a fault detection stage for leakage current.

Components of the surgical system 20 relevant to reducing or eliminating leakage current 62 are depicted in FIGS. 4-7. FIGS. 4, 5 and 7 depict embodiments with passive (first) and active (second) leakage current cancellation sources 68, 74, respectively.

The second current source 74 receives two inputs, namely, a sensed signal 110 and a target value 114. In one embodiment, shown in FIG. 4, a transformer 106 is used to sense residual leakage current 62 in the drive signal 105 and generate the sensed signal 110. Transformer 106 comprises the drive path 104 as a primary winding. In other words, the primary winding of the transformer 106 comprises the high-side voltage conductor 100 and the low-side voltage conductor 102. Transformer 106 has a secondary winding implementing a sensor 108.

The sensor 108 senses common mode current in the drive path 104 and outputs the sensed signal 110 indicative of the common mode current to the second current source 74. The common mode current provides some indication or relationship to the leakage current 62. Mainly, the high-side voltage conductor 100 conducts current to the surgical device and the low-side voltage conductor 102 conducts current away from the surgical tool 28. These currents 100 and 102 are ideally, equal in magnitude and opposite in polarity. When leakage current 62 is present, the magnitude of the current on the high-side voltage conductor 100 will be different from the magnitude of the current on the low-side voltage conductor 102. This difference in current is the common mode current. Common mode current is a measurement of the current flowing in a single direction. When a common mode current is present across the drive path 104, it generates a magnetic field that is sensed by the secondary winding, i.e., sensor 108. In this embodiment common mode current is directly related to leakage current 62 of the drive signal 105 because common mode current will only be present when some amount of current is lost between the high-side voltage conductor 100 and the low-side voltage conductor 102. If no leakage current 62 exists, the high-side voltage conductor 100 will have current that is equal and opposite to the current across the low-side voltage conductor 102. In this instance both common-mode current and leakage current 62 in the powered surgical tool system is 0 or substantially 0.

In FIG. 5, the sensor 108 is replaced by sensor 126, which is shown as a capacitor. Sensor 126 senses voltage on the low-side voltage conductor 102 of the drive path 104. When no leakage current 62 is present the voltage on the low-side conductor will be 0 volts, or approximately 0 volts, relative to power source 82.

In an embodiment where the shield 99 is also electrically connected to the low-voltage conductor 102 in the surgical tool 28, common mode current is instead the difference between the current on the high-voltage conductor 100 and the low voltage conductor 102 plus the shield 99.

In FIGS. 4, 5 and 7, leakage current 62 is illustrated as a small current opposing the portion of the drive signal 105 on the low-voltage conductor 102 in order to represent current that has escaped the drive signal 105 and passed to ground through another path. This leakage current 62 is the result of current that may be lost in a number of ways and locations throughout system to, including capacitive coupling between elements of the system 20 and/or leakage of current through the patient. The leakage current 62 could be illustrated anywhere that unintended flow of current is occurring. In some instances the first cancellation current 80 and second cancellation current 122 may result in leakage current 62 that flows in a opposite direction to the direction of the leakage current 62 shown in the Figures.

The sensed signal 110 may be modified by one or more gain devices, depicted in FIGS. 4, 5 and 7 as amplifier 112. The sensed signal 110 is inputted to the second current source 74 for determining the second cancellation current 122.

A second input to the second current source 74 is the target value 114, shown to the right in FIGS. 4, 5 and 7. The sensed signal 110 and the target value 114 are fed into the summing amplifier 118 with amplification 120 to output the second cancellation current 122. In FIGS. 4 and 7, the target value 114 is a target current for comparing to the sensed signal 110, which is used to determine the second cancellation current 122. In this example, the target current may be, for example, 0 amps, representing ideal conditions for elimination of leakage current. In FIG. 5, the target value 114 is a target voltage, which may be set to 0 volts, for example, also representing ideal conditions for elimination of leakage current. Other target values 114 besides those described herein are contemplated and may be utilized.

As shown in FIGS. 4, 5 and 7, a power source drives the second current source 74. In the examples shown, this is the same power source 82 that energizes the transformer 90. Additional aspects of the power source 82 as it relates to the second current source 74 are described below. Alternatively, the power source that powers the second current source 74 may be different from power source 82. The target value 114 may have some amount of DC offset because DC power source 82 is used to energize the second cancellation current 122. The target value 114 may be modified by gain device 116 and then used as an input into summing amplifier 118 with additional amplification stage 120. The summing amplifier 118 with amplification 120 determines the difference between the target value 114 and the sensed signal 110. The summing amplifier 118 with amplification 120 then outputs the second cancellation current 122.

Before the second cancellation current is injected into the drive path 104, a capacitor 124 may be used to block any DC component of the second cancellation current 122 from entering the drive path 104. In some embodiments, the capacitor 124 uses low capacitance.

This second cancellation current 122 cancels at least some of the residual leakage current 62 that remains when the first leakage current cancellation 80 is injected. Regardless of the type of sensor 106, 126 used, the second cancellation current 122 will both modify the magnitude of the current on the low-side voltage conductor 102 so that it more closely matches the magnitude of the current on the high-side voltage conductor 100, and will bring the voltage relative to the power source 82 closer to 0 volts.

Non-disclosed equivalents of the active current leakage cancellation techniques shown in FIGS. 4, 5 and 7 are fully contemplated. The schematic representations shown in FIGS. 4, 5 and 7 may include additional or different components from those specifically shown while still producing suitable cancellation currents, as contemplated.

B. Open Loop Control Current Cancellation Control

FIG. 6 shows another embodiment of the second current source 74 used to generate the second current cancellation current 122. In this embodiment, a measurement from the drive signal 105 is not utilized. Instead, a sensor 130 is included to measure the AC signal generated by transformer 90. In one example, the AC signal is a voltage of the surgical tool 28 hand piece. The sensor 130 could be part of or in addition to transformer 90. In the embodiment in FIG. 6, the sensor 130 is transformer winding.

Sensor 130 measures the AC signal generated across transformer 90 and sends the sensed signal to a gain stage 132 that is configured to scale the AC signal from the sensor 130. The variable gain device 132 may be part of the second current source 74, or may be separate therefrom.

A selection interface 134 is coupled to the second current source 74 and to the gain stage 132. The selection interface 134 is configured to enable selection of one of a plurality of leakage current adjustment settings. The leakage current adjustment settings provide user-selectable fine-tuning cancellation of the leakage current 62. The leakage current adjustment settings can be saved in a look-up table in the control console 22 memory.

In the example shown in FIG. 6, the selection interface 134 is a potentiometer, which may be adjustable circuitry or a digital potentiometer controlled by software. The selection interface 134 may also be implemented by a user interface on the display 34 of the control console 22. Other types of selection interfaces for enabling selection of leakage current adjustment settings are contemplated.

The selection interface 134 enables easier adjustment of positive or negative leakage currents. Adjustments may be made to enable the control console 22 to meet the IEC 60601, or any additional or different standard for leakage current.

The selection interface 134 is coupled to the sensor 130 through the first gain stage 132. The selection interface 134 receives a scaled version of the AC signal from the first gain stage 132. The selection interface 134 is coupled to a variable gain amplifier 138 that can adjust the gain from −1 to +1 based on the selection interface 134 adjustment setting. In instances where the selection interface 134 is a potentiometer, the variable gain amplifier 138 comprises an output 136 interfacing with the potentiometer to variably operate the same.

In one embodiment, the selection interface 134 is adjusted as part of the manufacturing process. This enables greater manufacturing tolerances and ensures that each control console 22 meets requirements to minimize leakage current.

The output of amplifier 138 is then fed to a power amplifier 140 that makes use of a power source, such as the power source 82 that powers the drive signal 105. In the alternative, the second current source 74 could use a separate power source. Amplifier 140 outputs the second cancellation current 122 into the drive signal path 104. The second cancellation current 122 is DC blocked by capacitor 124 before being injected into the drive signal path 104.

As with the embodiments described in the previous section in relation to FIGS. 4, 5 and 7, the second cancellation current 122 generated in the embodiment of FIG. 6 may be utilized in conjunction with the first cancellation current 80 generated by the first current source 68 to thereby provide fine tuning for cancellation of the leakage current 62.

Non-disclosed equivalents of the active current leakage cancellation techniques shown in FIG. 6 are fully contemplated. The schematic representation shown in FIG. 6 may include additional or different components from those specifically shown while still producing suitable cancellation currents, as contemplated.

C. Variable Power Source for Second Current Source

For any of the embodiments described herein, and shown in FIG. 4-7, the power source 82 coupled to the primary winding 84 of the transformer 90 may be a variable power source. According to one example, the power source 82 has a variable output DC voltage level that can be set. In one embodiment, this voltage is between 25 and 250 VDC. Other types of power sources with or without variable voltage levels may also be used. The voltage of the signal out of the power source 82 is set based on a power source control signal applied to the power source 82. The power source 82 may apply a DC input signal to a center tap of the primary winding 84 of the transformer 90. The DC input signal from power source 82 may have a potential that varies. Specifically, the potential of this input signal may be set to vary as a function of the potential of the drive signal 105 that is to be applied to the power generator 27 of the surgical tool 28.

This variable power source 82 may be utilized to energize, drive or otherwise provide input to any of the second current sources 74 shown throughout the Figures. The second current source 74 may be coupled to the path of the drive signal 104 and coupled to the variable power source 82. The variable power source 82 is configured to energize the current source 74 and the current source 74 (energized by the variable power source 82) is configured to generate the cancellation current 122 to inject into the path 104 of the drive signal to cancel leakage current of the drive signal.

Specifically, the DC input signal from power source 82 applied to the primary winding 84 may also be used as an input into one or more of the amplifiers 120 or 140 of the second current source 74, shown in FIGS. 4, 5, and 7. Specifically, this DC input signal may be used as the positive voltage to facilitate the amplification of the signal produced by the second current source 74 to ensure the signal is at the correct voltage. In these versions, this DC signal may also be applied to the second current source 74 as an input signal, shown in FIGS. 4, 5, and 7 as Power Source 82 feeding into the stage that generates target value 114. The second current source 74 includes a feedback sub-circuit that adjusts the target value 114 from this variable power source 82 so the signal does not drift as a result of changes in the DC positive voltage applied to the one or more amplifiers. In the embodiment shown in FIG. 6, the second current source 74 is energized by the variable power source 82 connected to amplifier 140.

The variable power source 82 drives the second cancellation current 122. In one embodiment, this is the same power source 82 that energizes the drive path 104 for the surgical tool 28. Using the same power source 82 provides benefit because the power needed to drive the second cancellation current 122 varies in proportion to the power of the drive signal 105. Alternatively, a separate power source may be used to drive the second leakage current source 74.

While reusing the variable power source 82 to energize the leakage current cancellation sources is advantageous, embodiments may include a separate power source to generate the second cancellation currents 122.

The variable power source 82 may have configurations and capabilities other than those shown in the Figures and described herein. Moreover, the variable power source 82 may be coupled to components of the control console 22 other than those shown in the Figures.

D. Fault Detection Techniques for Leakage Current

FIG. 7 shows the same components as FIG. 4 with the addition of a fault detection stage 144, which can be implemented by circuitry and/or software.

The fault detection stage 144 is coupled to the sensor 106 or alternatively sensor 126 from FIG. 5. The fault detection stage 144 is configured to receive the sensed signal 110 from the sensor 106, 126 and to generate a fault detection signal 158 for detection of a fault condition related to leakage current 62.

If the sensed signal 110 indicates levels of leakage current 62 beyond a specified threshold, it could be due to a fault in the system 20, such as a short or a connection of the patient to ground. When leakage current 62 is excessive, the fault detection stage 144 triggers the fault detection signal 158 at a GPIO (general purpose input/output) line.

A controller 160 is coupled to the fault detection stage 144, e.g., at the GPIO line, and is configured to receive the fault detection signal 158 from the fault detection stage 144 and to determine the fault condition related to leakage current 62. The controller 160 may have one or more microprocessors for processing instructions or for processing an algorithm stored in memory to control operation of the control console 22. Additionally or alternatively, the controller 160 may comprise one or more microcontrollers, field programmable gate arrays, systems on a chip, discrete circuitry, and/or other suitable hardware, software, or firmware that is capable of carrying out the functions described herein. The fault detection stage 144 and controller 160 may be combined or separate elements.

The fault detection stage 144 is configured to sense presence of the fault detection signal 158 for a predetermined period of time and to send the fault detection signal 158 to the controller 160 when the predetermined period of time is reached. The fault detection stage 144 may do so to ensure that persistent fault is detected and to avoid false alarms based on negligible or intermittent signal spikes.

The controller 160 receives the fault detection signal 158 from the GPIO line and is configured to compare the fault detection signal 158 to a target value to determine the fault condition. The controller 160 can decrease or terminate power to the surgical tool 28 in response to determination of the fault condition. The controller 160 may trigger other responses for the control console 22 or surgical tool 28 other than those described herein.

Figure 8:
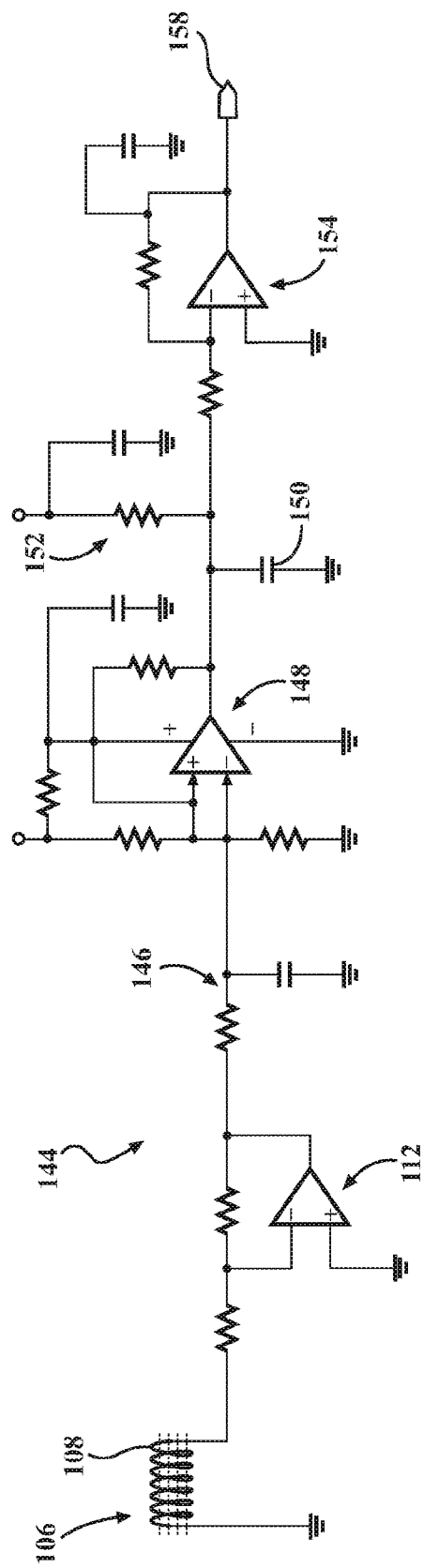
FIG. 8 is a schematic diagram of circuitry included in the fault detection stage according to one embodiment.

FIG. 8 shows one embodiment of the fault detection stage 144. In certain embodiments, the fault detection stage 144 only becomes active when the sensed common mode current or the low-side voltage surpasses a specified level. The sensed signal 110 may be modified by amplifier 112. This amplifier 112 may be the same as the first gain stage used to generate the second cancellation current 122 or it may be a separate gain device. The sensed signal 110 is then fed to low pass filter 146 and rectifier 148. The low pass filter 146 will remove higher frequency signals beyond a specified threshold. Low pass filter 146 may also attenuate the signal, if it is relatively close to the filter frequency. A gain device, depicted as amplifier 148, may be used to change the amplitude of the sensed signal 110 in response to any attenuation. During a fault condition, sensed signal 110 will pulse every drive cycle (e.g. when the drive signal 105 is at maximum amplitude the common mode current sensed by sensor 108 will be as a maximum, when the drive signal 105 is at a minimum common mode current will approach 0). A filter comprising capacitor 150 and resistor 152 is put in place to hold the fault condition at its maximum level between pulses. The RC time constant of the filter is the capacitance of capacitor 150 multiplied by the resistance of resistor 152. The fault signal is then output to an inverter 154, which inverts the applied signal to output the fault signal 158 to controller 160. The controller 160 monitors the signal and when fault condition exists for a specific period controller 160 can take appropriate action with the system as necessary. Actions taken by controller 160 include alerting the operator of the surgical tool 28 via the display 34, reducing the power output by power source 82, and/or shutting off power to the surgical tool 28.

The fault detection stage 144, controller 160, and components thereof may be different from that described herein while still realizing the capabilities for detecting leakage current faults, as described herein.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A control console for supplying a drive signal to a surgical tool, the control console comprising:
   a transformer comprising a primary winding and a secondary winding, the primary winding being configured to receive an input signal from a power source and to induce the drive signal in the secondary winding to supply the drive signal to the surgical tool;
   a first current source comprising a leakage control winding coupled to a path of the drive signal, wherein the primary winding is configured to induce a first cancellation current in the leakage control winding to inject into the path of the drive signal to cancel a first portion of leakage current of the drive signal;
   a sensor coupled to the path of the drive signal, wherein the sensor is configured to output a sensed signal to provide feedback related to the leakage current; and
   a second current source coupled to the path of the drive signal and to the sensor, the second current source being configured to receive the sensed signal and to determine a second cancellation current to inject into the path of the drive signal to cancel a residual portion of the leakage current based on the sensed signal.

2. The control console as claimed in claim 1, wherein the primary winding, the leakage control winding, and the secondary winding are configured to collectively generate a capacitance between the leakage control winding and the secondary winding.

3. The control console as claimed in claim 1, wherein the second current source is also energized by the power source.

4. The control console as claimed in claim 1, wherein the second current source is configured to receive a target value as inputs and to determine the second cancellation current to inject into the path of the drive signal to cancel the residual portion of the leakage current based on the sensed signal and the target value.

5. The control console as claimed in claim 4, wherein the second current source comprises a gain device coupled to the sensor, and the gain device is configured to determine a difference between the sensed signal and the target value and to determine the second cancellation current based on the difference.

6. The control console as claimed in claim 5, wherein the second current source further comprises a capacitor coupled to the gain device, the capacitor isbeing configured to block the DC component of the second cancellation current.

7. The control console as claimed in claim 4, wherein the sensor is configured to sense a common-mode current of the drive signal and to output the common-mode current of the drive signal as the sensed signal received by the second current source, the common-mode current being related to the leakage current of the drive signal, and the target value received by the second current source defines a target current.

8. The control console as claimed in claim 7, wherein the path of the drive signal comprises a high voltage conductor and a low voltage conductor, the sensor is defined as a transformer winding disposed around both the high and low voltage conductors, and the transformer winding is configured to output the common-mode current of the drive signal.

9. The control console as claimed in claim 4, wherein the path of the drive signal comprises a high voltage conductor and a low voltage conductor, the sensor is coupled to the low voltage conductor and is configured to sense a voltage from the low voltage conductor and to output the voltage as the sensed signal received by the second current source, and the target value received by the second current source defines a target voltage.

10. The control console as claimed in claim 9, wherein the sensor is a capacitor.

11. The control console as claimed in claim 9, wherein the second current source is configured to inject the second cancellation current into the low voltage conductor.

12. The control console as claimed in claim 1, wherein the sensor is configured to sense a current of the drive signal and to output the current of the drive signal as the sensed signal.

13. The control console as claimed in claim 1, further comprising:
   a fault detection stage coupled to the sensor and being configured to receive the sensed signal and to generate a fault detection signal responsive to detection of a fault condition related to the leakage current and
   a controller coupled to the fault detection stage and configured to receive the fault detection signal from the fault detection stage, determine the fault condition based on the fault detection signal received from the fault detection stage, and decrease or terminate power to the surgical tool in response to determination of the fault condition.

14. A control console for supplying a drive signal to a surgical tool, the control console comprising:
   a transformer comprising a primary winding and a secondary winding and with the primary winding configured to receive an input signal from a power source and to induce the drive signal in the secondary winding to supply the drive signal to the surgical tool;
   a first current source comprising a leakage control winding coupled to a path of the drive signal and with the primary winding configured to induce a first cancellation current in the leakage control winding to inject into the path of the drive signal to cancel leakage current of the drive signal;
   a sensor configured to sense a characteristic of the input signal and to output a sensed signal related to the characteristic of the input signal;
   a second current source coupled to the path of the drive signal;
   a variable gain device coupled to the sensor and to the second current source; and
   a selection interface coupled to the second current source and to the variable gain device and being configured to enable selection of one of a plurality of leakage current adjustment settings and to provide the selected leakage current adjustment setting to the variable gain device;
   wherein the variable gain device is configured to receive the sensed signal and to modify the sensed signal based on the selected leakage current adjustment setting; and
   wherein the second current source is configured to generate a second cancellation current based on the modified sensed signal from the variable gain device and to inject the second cancellation current into the path of the drive signal to cancel leakage current of the drive signal.

15. The control console as claimed in claim 14, wherein the sensor is a transformer winding.

16. The control console as claimed in claim 14, wherein the selection interface is a potentiometer.

17. A control console for supplying a drive signal to a surgical tool, the control console comprising:
a variable power source;
a transformer comprising a primary winding and a secondary winding, with the primary winding coupled to the variable power source and configured to receive an input signal from the variable power source and to induce a drive signal in the secondary winding to supply the drive signal to the surgical tool;
a sensor coupled to a path of the drive signal and configured to output a sensed signal related to leakage current of the drive signal; and
a current source coupled to the path of the drive signal, the sensor and the variable power source, wherein the variable power source is configured to energize the current source, and the current source is configured to receive the sensed signal and a target value as inputs, determine a difference between the sensed signal and the target value, and generate a cancellation current to inject into the path of the drive signal to cancel the leakage current of the drive signal based on the difference.

18. The control console as claimed in claim 17, wherein the current source comprises a gain device coupled to the sensor, the gain device being configured to receive the sensed signal and the target value as inputs and to determine the difference between the sensed signal and the target value, and determine the cancellation current based on the difference.

19. The control console as claimed in claim 17, further comprising:
a sensor configured to sense a characteristic of the input signal and to output a sensed signal related to the characteristic of the input signal;
a variable gain device coupled to the sensor and to the current source; and
a selection interface coupled to the current source and to the variable gain device and being configured to enable selection of one of a plurality of leakage current adjustment settings and to provide the selected leakage current adjustment setting to the variable gain device;
wherein the variable gain device is configured to receive the sensed signal and to modify the sensed signal based on the selected leakage current adjustment setting; and
wherein the current source is configured to generate the cancellation current based on the modified sensed signal from the variable gain device.

20. The control console as claimed in claim 17, wherein the variable power source energizes a source for the target value and the variable power source is configured to provide the target value with a DC offset in addition to an AC value.

\* \* \* \* \*